United States Patent [19]

Iversen

[11] 4,374,527

[45] Feb. 22, 1983

[54] BODY STIMULATION LEAD

[75] Inventor: Alfred A. Iversen, Minnetonka, Minn.

[73] Assignee: Medtronic, Inc., Minneapolis, Minn.

[21] Appl. No.: 926,100

[22] Filed: Jul. 19, 1978

[51] Int. Cl.³ .............................................. A61N 1/04
[52] U.S. Cl. ................. 128/785; 128/419 P; 128/786
[58] Field of Search ................ 128/303 R, 404, 418, 128/419 P, 784–785, 786

[56] References Cited

U.S. PATENT DOCUMENTS

| 2,756,752 | 7/1956 | Scherlis | 128/303 R |
| 3,472,234 | 10/1969 | Tachick | 128/418 |
| 3,534,733 | 10/1970 | Phipps | 128/418 |
| 3,937,225 | 2/1976 | Schramm | 128/418 |
| 4,044,774 | 8/1977 | Corbin et al. | 128/404 |
| 4,135,518 | 1/1979 | Dutcher | 128/419 P |

OTHER PUBLICATIONS

Lui "Surgery", vol. 61, No. 3, Mar. 1967, pp. 380–381.

Primary Examiner—William E. Kamm
Attorney, Agent, or Firm—Schroeder, Siegfried, Vidas, Steffey & Arrett

[57] ABSTRACT

An improved body stimulation lead wherein the electrode is isolated from extraneous forces imparted to the lead body. In a preferred embodiment, a plurality of lobes are formed in the lead body, the lobes being engageable with body tissue to maintain the position of the electrode and being deformable in response to extraneous forces to minimize the influence of such forces on the position of the electrode. In addition, the lead conductor is formed as a space-wound coil which provides additional stress relief. A stylet is insertable within the coil to temporarily straighten the lobes and to provide sufficient stability to the lead body for placement of the lead.

29 Claims, 5 Drawing Figures

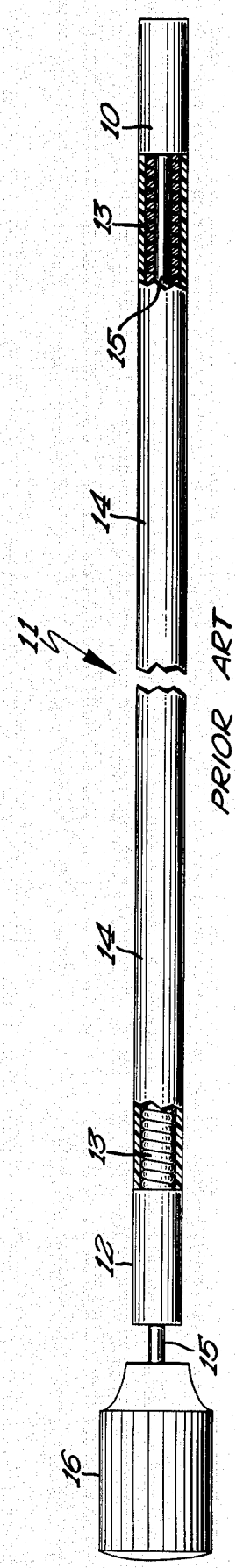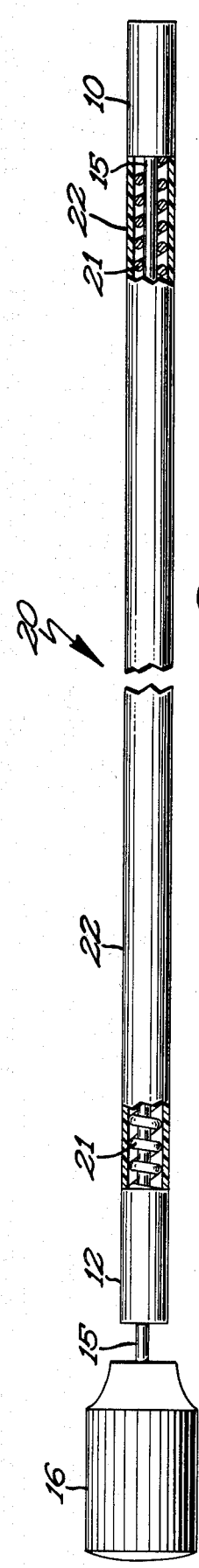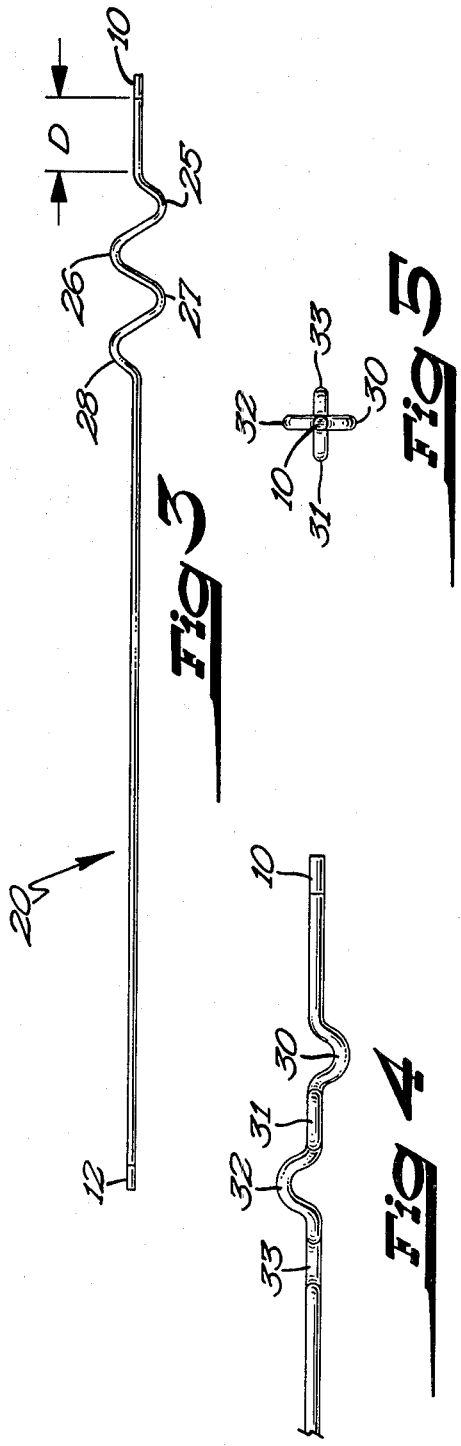

BODY STIMULATION LEAD

BACKGROUND OF THE INVENTION

Electrical stimulation of the body is an increasingly important medical procedure. For example, the circumstances in which the well known cardiac pacemaker is employed have expanded considerably. Other electrical stimulators are similarly gaining in acceptance.

A difficulty encountered in many stimulating contexts is the requirement that the electrode be precisely positioned and that that position be maintained. For example, nerve stimulation is often selective requiring precision in the placement of the electrode. A later movement of the electrode is destructive to the effectiveness of the stimulation and may render the stimulation totally ineffective.

In some contexts, it is possible to secure the electrode in the desired position. In others, securement is not possible. In all contexts, forces acting on the lead may be transmitted by the lead to the electrode. Particularly in those contexts where the electrode is not secured, such forces have a tendency to displace the electrode. Such forces are commonly experienced and result from such factors as body movement, muscle contraction, etc.

Many surgeons have evolved their own techniques for anchoring a lead to reduce the transmittal of a displacing force to an electrode. For example, it is known that many surgeons employ a deformable surgical clip to anchor a body stimulator lead. The clip is positioned around and drawn down on the lead. The clip also engages body tissue. In this manner the lead is secured to the body tissue. Other techniques employ the use of a band positioned around the lead body as a suturing device.

An improvement to the techniques described above is disclosed in U.S. Patent Application Ser. No. 926,105 filed July 19, 1978, now abandoned for Lead Anchoring Device, in the name of Duane J. Zytkovicz, which is commonly owned with the present invention. In the referenced application, a simple molded device is disclosed which can be positioned anywhere along the lead body and which securely engages the lead body and may be easily anchored to body tissue thereby providing a simple and reliable anchoring device. However, use of this device, and the techniques described above, may not be adequate in many situations. For example, in those contexts where it is not possible to secure the electrode it is unlikely that the lead can be anchored at a position sufficiently close to the electrode to adequately isolate the electrode from extraneous forces imparted to the lead body. Therefore, while lead anchoring is a helpful procedure in maintaining the position of an electrode, it, in itself, is not always adequate.

SUMMARY OF THE PRESENT INVENTION

The present invention provides a system for isolating an electrode from extraneous forces imparted to the lead and is particularly useful in those contexts where it is not possible or desireable to use a lead anchoring device in close proximity to the electrode. However, the system of the present invention may be employed in conjunction with an anchoring device spaced from the electrode site. In a preferred embodiment, a plurality of lobes are formed in the lead body proximate to but spaced from the electrode, the lobes being engageable with body tissue to maintain the position of the electrode and being deformable in response to extraneous forces to minimize the influences of such forces on the position of the electrode. Additionally, the lead conductor may be formed as a space-wound coil which provides additional stress relief over that of the prior art close-wound coil. A stylet is employed to temporarily straighten the lobes and provide sufficient stability to the lead for placement.

BRIEF DESCRIPTION OF THE DRAWINGS

FIG. 1 is a partial cut-away of a typical prior art lead.

FIG. 2 is a partial cut-away of a preferred embodiment of the present invention.

FIG. 3 illustrates a preferred configuration of the lead of the present invention.

FIG. 4 illustrates another configuration of the lead of the present invention.

FIG. 5 is an end view of the embodiment of FIG. 4.

DETAILED DESCRIPTION OF THE DRAWINGS

The system of the present invention is applicable to any environment wherein it is necessary or desireable to isolate the electrode from extraneous forces imparted to the lead and in particular those environments wherein the electrode is positioned in a body passage or cavity. For example, a lead and implant procedure for dorsal column stimulation via a lead positioned in the epidural space is disclosed in U.S. Pat. No. 4,044,774 issued Aug. 30, 1977 to Terry Corban and Duane J. Zytkovicz for Percutaneously Inserted Spinal Cord Stimulation Lead, which patent is owned by the assignee of the present invention and which is hereby incorporated by reference. Within the environment of the incorporated patent, electrode position is critical to the effectiveness of the stimulation. Further, there have been several instances of electrode movement after implant, a fact that is a significant factor in the decision to undergo the procedure. The procedure is highly beneficial in many instances so long as the proper electrode position is maintained. The system of the present invention is applicable to the environment of the incorporated patent and other stimulating contexts.

Referring now to FIG. 1, there is shown a typical prior art lead that may be employed for dorsal column stimulation, for example, including an electrode 10, lead body 11 and connector 12. The lead body 11 is formed by a conductor in the form of a coil 13 extending between the electrode 10 and connector 12 and an insulating sheath 14. The lead illustrated in FIG. 1 is similar to that illustrated as prior art in FIG. 1 of the incorporated patent, the primary difference being in the coil windings. FIG. 1 of the incorporated patent appears to illustrate a space-wound coil which forms a portion of the present invention. In fact, however, FIG. 1 hereof more accurately illustrates the prior art coil as a close-wound coil, the drawings of the incorporated patent merely illustrating the fact that the conductors are coils without setting forth any advantage in the use of a space-wound coil. For the purpose of this specification, a space-wound coil is a coil in which there is space between adjacent coil windings while a close-wound coil is a coil in which there is little or no space between adjacent coil windings.

Electrode 10 and connector 12 mechanically and electrically engage the coil 13, in known manner. Also, the positioning of the sheath 14 around the coil 13 is known to the prior art. A stylet 15 is employed to provide stability to the lead during placement and is provided with a handle 16, in known manner.

Referring now to FIG. 2, there is illustrated a preferred embodiment of the present invention including an electrode 10, connector, 12, stylet 15 and its handle 16 which may be identical to that of the prior art lead of FIG. 1. However, the lead body 20 is formed of a space-wound coil 21 and a sheath 22 of high durometer, the coil 21 and sheath 22 providing the lead of the present invention with greater flexibility than prior art leads. Accordingly, the lead of the present invention will more easily deflect, elongate, and compress than typical prior art leads. In essence, space-wound coil 21 and high durometer sheath 22 provide stress relief in that they will physically respond to a force applied to the lead body with less transmittal of that force to the electrode 10 than a prior art lead. Accordingly, the lead body 20 of the present invention has a tendency to isolate the electrode from forces imparted to the lead by the virtue of the greater strain or deformation in response to those forces.

An additional isolating mechanism forming a part of the present invention is illustrated in FIG. 3. In FIG. 3, the lead body is provided with lobes 25-28 proximate the electrode 10 but spaced therefrom by the distance D. The lobes 25-28 are engageable with the surrounding tissue of a body passage or cavity to resist movement of the electrode. Additionally, in many body environments fibrosis will form around the lead, the fibrosis cooperating with the irregular conformation of the lobes 25-28 to further resist movement of the electrode to a greater degree than would fibrosis development about a straight lead.

In addition to maintaining the position of electrode 10 by engagement of body tissue, the lobes 25-28 provide additional significant isolation of the electrode from a force imparted to the lead body 20 by deforming in response to a force imparted to the lead body. That is, while the lead body itself is more flexible than prior art leads, the lobes 25-28 enhance that flexibility by superimposing an additional strain on the response of the lead body itself. The combination of the space-wound coil 21, high durometer sheath 22, tissue engagement by lobes 25-28 and response of the lobes 25-28 to an extraneous force provide effective isolation of the electrode 10 from a force applied to the lead body 20 thereby minimizing the influence of those forces on the position of the electrode. Lobes 25-28 may be "cold formed" by hand or by a suitable automated device and may take any suitable configuration. Sheathing materials of high durometer are known which will assume the lobe configuration with proper treatment such that the sheath does not interfere with the maintenance of the lobe configuration. It has been found that four lobes of generally semicircular configuration, as illustrated in FIG. 3, provide adequate stability in most circumstances. The lobes may be temporarily straightened by the insertion of the stylet 15, this straightening of the lobes and the additional stability provided by the stylet assisting during placement of the lead. On removal of the stylet, the lobes 25-28 will again assume the configuration illustrated in FIG. 3.

It has been established, that if the lobe closest to the electrode 10 (lobe 25) is too close to the electrode, it could effect the position of electrode 10 as that lobe assumes the lobe configuration on removal of the stylet. It appears that the closest lobe should be no closer to the electrode than about twenty times the diameter of the electrode body. Additionally, if the closest lobe is too far from the electrode, the lead body between the lobe and electrode is unstable. It appears that the closest lobe should be no further from the electrode than about forty times the diameter of the electrode body, and, preferably, the closest lobe should be approximately 25 times the diameter of the lead from the electrode. Within the dorsel column electrode of the incorporated patent having an approximate diameter of 0.10 cm, the first lobe should be no closer than two centimeters from the electrode, no further than four centimeters from the electrode, and, preferably, should be approximately 2.5 centimeters from the electrode.

Many modifications and variations of the present invention are possible in light of the above teachings. For example, FIGS. 2 and 3 illustrate what is presently considered to be the best mode for use within the environment of the incorporated patent. However, other lobe configurations and numbers of lobes may be employed without departing from the scope of the present invention. For example, FIGS. 4 and 5 illustrate a lead including lobes 30-33, FIG. 5 being an end view of FIG. 4. Lobes 30 and 32 extend in opposing directions within the plane of the drawing sheet. Lobes 31 and 33 extend in opposing directions in a plane perpendicular to the plane of the drawing sheet, lobe 31 extending outwardly from the sheet and lobe 33 extending inwardly from the sheet. Thus, any configuration of lobes in any special relation to each other are to be considered as being within the scope of the present invention. It is therefore to be understood that, within the scope of the appended claims, the invention may be practiced other than as specifically been described.

What is claimed is:

1. In a body stimulator of the type having electrode means, connector means and lead body means extending between said electrode means and connector means, said lead body means including conductor means and conductor means insulating means, the improvement wherein said lead body means comprises means for deforming in compression and elongation in response to extraneous forces imparted to said lead body means to isolate said electrode means therefrom, said deforming means comprising lobe means formed within said lead body means.

2. The lead of claim 1 wherein said lobe means are proximate to but spaced from said electrode means.

3. The lead of claim 2 wherein said lobe means comprises a plurality of lobes formed within said lead body means.

4. The lead of claim 3 wherein the lobe closest to the electrode means is no closer to the electrode means than about twenty times the diameter of the electrode body means and no further from the electrode body means than about forty times the diameter of the electrode body means.

5. The lead of claim 4 wherein said lobe closest to said electrode means is approximately 25 times the diameter of said lead means from said electrode means.

6. The lead of claim 3 wherein the lobe closest to the electrode means is no closer to the electrode means than about 2 cm and no further from the electrode means than about 4 cm.

7. The lead of claim 6 wherein said lobe closest to said electrode means is approximately 2.5 cm from said electrode means.

8. The lead of claim 2 wherein said lobe means comprises four generally semicircular lobes.

9. The lead of claim 1 wherein said deforming means further comprises space-wound coil means forming said conductor means.

10. The lead of claim 9 further comprising stylet means insertable through said coil means for temporarily straightening said lobes.

11. The lead of claim 9 wherein said lobe means are formed in said coil means.

12. The lead of claim 1 wherein said deforming means comprises space-wound coil means forming said conductor means.

13. In a body stimulator lead of the type having electrode means, connector means and lead body means extending between said electrode means and connector means, said lead body means including conductor means and conductor means insulating means, the improvement wherein said lead body means comprises strain means responsive to forces imparted to said lead body means for deforming in compression and elongation to minimize the influence of said forces on the position of said electrode means, said strain means comprising lobe means formed within said lead body means.

14. The lead of claim 13 wherein said lobe means comprises a plurality of lobes formed within said lead body means.

15. The lead of claim 14 wherein said lobe closest to said electrode means is approximately 25 times the diameter of said lead means from said electrode means.

16. The lead of claim 15 wherein said lobe closest to said electrode means is approximately 2.5 cm from said electrode means.

17. The lead of claim 13 wherein said lobe means comprises four generally semicircular lobes.

18. The lead of claim 13 wherein said strain means further comprises space-wound coil means forming said conductor means.

19. The lead of claim 18 further comprising stylet means insertable through said coil means for temporarily straightening said lobes.

20. The lead of claim 18 wherein said lobe means are formed in said coil means.

21. The lead of claim 13 wherein said lobe means comprise means for engaging body tissue to further minimize the influence of said forces on the position of said electrode means.

22. The lead of claim 13 wherein said lobe means are proximate to but spaced from said electrode means.

23. The lead of claim 22 wherein the lobe closest to the electrode means is no closer to the electrode means than about twenty times the diameter of the electrode body means and no further from the electrode body means than about forty times the diameter of the electrode body means.

24. The lead of claim 22 wherein the lobe closest to the electrode means is no closer to the electrode means than about 2 cm and no further from the electrode means than about 4 cm.

25. The lead of claim 13 wherein said strain means comprises space-wound coil means forming said conductor means.

26. In a body stimulator lead of the type having electrode means, connector means and lead body means extending between said electrode means and connector means, said lead body means including conductor means and conductor means insulating means, the improvement wherein said lead body means comprises lobe means of irregular conformation formed within said lead body means for maintaining the position of said electrode means, said lobe means comprising means for engaging body tissue to resist movement of said electrode means and further comprising means for deforming in response to an extraneous force imparted to said lead body means.

27. The lead of claim 26 wherein said love means comprises four generally semicircular lobes.

28. The lead of claim 26 wherein said lobe means are proximate to but spaced from said electrode means.

29. The lead of claim 26 wherein said lobe means comprises a plurality of lobes formed within said lead body means.

* * * * *

UNITED STATES PATENT AND TRADEMARK OFFICE
CERTIFICATE OF CORRECTION

PATENT NO. : 4,374,527
DATED : February 22, 1983
INVENTOR(S) : Alfred A. Iversen It is certified that error appears in the above-identified patent and that said Letters Patent are hereby corrected as shown below:

Column 6, line 35, delete "love" and insert - lobe -

*Signed and Sealed this*

*Twenty-sixth* Day of *July 1983*

[SEAL]

*Attest:*

GERALD J. MOSSINGHOFF

*Attesting Officer*     *Commissioner of Patents and Trademarks*